United States Patent [19]

Utsugi

[11] Patent Number: 4,699,482
[45] Date of Patent: Oct. 13, 1987

[54] OPTHALMOSCOPIC SYSTEM

[75] Inventor: Katsuhiko Utsugi, Tsuchiura, Japan

[73] Assignee: Utsugi Optical Laboratory Inc., Tsuchiura, Japan; a part interest

[21] Appl. No.: 816,982

[22] Filed: Jan. 7, 1986

Related U.S. Application Data

[63] Continuation of Ser. No. 505,495, Jun. 17, 1983, abandoned.

[30] Foreign Application Priority Data

Jun. 23, 1982 [JP] Japan ............................. 57-106897

[51] Int. Cl.$^4$ ........................... A61B 3/14; A61B 3/10; G03B 29/00
[52] U.S. Cl. ...................................... 351/206; 354/62
[58] Field of Search ............... 351/205, 206, 207, 208, 351/221; 354/62

[56] References Cited

U.S. PATENT DOCUMENTS 4,259,948  4/1981  Urban ............................. 351/206 X Primary Examiner—Rodney B. Bovernick
Attorney, Agent, or Firm—Oblon, Fisher, Spivak, McClelland & Maier

[57] ABSTRACT

An ophthalmoscopic system having in combination, a intraocular illumination light source, a multitude of light transfer fibre optics regularly arranged in vertical and horizontal rows to project the illuminant light ray from said light source into an eye in the form of a multitude of discrete illuminant light points, a multitude of light-receiving fibre optics regularly arranged in vertical and horizontal rows alternately with said rows of the light transfer fibre optics to receive the reflections of the projected light points, an image receiver connected to said light-receiving fibre optics for converting a transmitted optical picture image into electric signals, and an output device electrically connected to the output terminal of said image receiver.

4 Claims, 3 Drawing Figures (a)

(b)

OPTHALMOSCOPIC SYSTEM

This application is a continuation of application Ser. No. 505,495 filed June 17, 1983, now abandoned.

BACKGROUND OF THE INVENTION (1) Field of the Invention

This invention relates to improvements in and relating to the ophthalmoscope to be used by oculists and physicians for intraocular inspection or observation.

(2) Description of the Prior Art

The intraocular inspection or observation has a great important in ophthalmological and internal examinations. In this connection, however, it is an usual experience that the conventional fundus camera or other ophthalmoscopic instrument which employs a single light source for transillumination is met by various difficulties during the inspection due to the peculiar optical characteristics of the eye. For example, in the case of inspection by a fundus camera, in order to make a full observation from the aspect of the illumination and observation systems, it becomes necessary to increase the intensity of transilluminant light from the single light source. However, on the contrary, the increase of the illumination light intensity increases the light reflections on the eyeball and as a result the observation is considerably obstructed by the reflected light. Therefore, there have thus far been made various technical improvements and proposals in connection with the fundus camera for attenuating the reflected light but none of them succeeded in arriving definite technical solutions to the above-mentioned problems, projecting excessive light into the patient's eye and failing to reply to the oculists' strong demand for improvements in this regard. On the other hand, the directoscope which exists also as an ophthalmoscopic instrument involves the same difficulties as the fundus cameras in principles, and at the present moment still has a number of technical problems yet to be solved.

Further, the so-called slit lamp microscope which is resorted to for intraocular observation is a system in which a light ray is projected through a slit lamp to form a narrow light ray. In this case, there is also a problem that, if the breadth of the light ray is broadened, the light reflection from the eye-ball becomes stronger and the image of the observing portion is blurred, in addition to problems in the operational aspect which need solutions.

SUMMARY OF THE INVENTION

With the foregoing situtations in view, the present invention has as its object the provision of a novel ophthalmoscopic system for intraocular observation or inspection, which is arranged to completely eliminate the adverse effects of the reflections of a projected light ray from the eyeball in an economical manner.

It is another object of the present invention to provide a novel ophthalmoscopic system for intraocular observation or inspection, which is extremely easy to handle and which can ensure stable ocular observation constantly without requiring special skills on the part of the observer.

It is still another object of the present invention to provide an ophthalmoscopic system of the sort mentioned above, which can arbitrarily adjust the intensity of projecting light, the angle of incident light, and the angle of receiving light.

According to the present invention, the above-mentioned objects are achieved by an ophthalmoscopic system which essentially comprises: a light source for intraocular illumination; a multitude of light transferring fibre optics arranged regularly in vertical and horizontal rows to project the light from the light source into an eye in the form of a multitude of discrete illuminant points; a multitude of light-receiving fibre optics arranged regularly in vertical and horizontal rows alternately with the light transferring fibre optics for receiving the reflections of the respective projected light points; an image receiver connected to the light-receiving fibre optics for converting a transmitted optical image into electric signals; and an output device electrically connected to the output terminal of the image receiver.

In this instance, the light source for transillumination should be of a visible light ray to permit intraocular observation or inspection by an oculist or a physician. Examples of such visible light source include: an incandescent illumination lamp with a luminous intensity of, for example, 30-50 W alone or in combination with a condenser lens; a laser light source such as a gas laser or a semiconductor laser in the range of visible ray; and a light source using a light emitting element such as laser diode (LD) and light emitting diode (LED). Whichever illumination light source is selected, it should be of a visible ray with a spectrum which has medically no possibility of imposing adverse affects on the patient's eye. Of these light sources, the incandescent lamp is used in ordinary cases, while the laser light and light emitting element are suitably applied in special ophthalmographic examinations. The end portions of the light transfer fibre optics to be connected to the light emitting element like the semiconductor laser are simply cut off or subjected to a lens-forming treatment beforehand, or combined with other optical lenses if necessary.

With regard to the light transfer fibre optics and light-receiving fibre optics, it is preferred to employ high quality fibre optics such as high quality optical plastic fibre, high quality optical glass fibre and high quality optical fibre with core and clad, and to arrange them regularly in alternate rows in the vertical and transverse directions.

The image converter is constituted, for example, by photosensitive elements with the function of photoelectric conversion or semiconductor image conversion elements. In the case of the semiconductor image conversion elements, it is preferably constituted by a chip with a matrix of electronic eyes each having the function of converting a received color quickly into an electric signal with high fidelity. The semi-conductor image conversion element may be of the known type, for instance, the MOS type semiconductor image converter HE 98221 (a product of Hitachi Seisakusho: 8.8 mm×6.6 mm scan area, 384×485 picture elements in horizontal and vertical directions, a size of 25.4×20.3 mm, sensitivity of 6.7 nA/ex, saturated signal current of 1.0 μA, 280×350 horizontal and vertical resolution, a monolithic color type).

The output system at least includes a video recording device such as a video tape recorder and a CRT display. If desired, the image conversion elements or the video recording device may be connected to a microcomputer or a personal computer which is provided with a CRT graphic display, a printer, a floppy disc capable of optical recording. If a suitable software is loaded on the microcomputer or personal computer, it becomes possible to computerize the judgement of the kind of the ocular disease, comparison with the past clinical data of the patient and assessment of the therapeutic results.

The above and other objects, features and advantages of the present invention will become apparent from the following description and the appended claims, taken in conjunction with the accompanying drawing which shows by way of example a illustrative embodiment of the invention.

Figure 1:
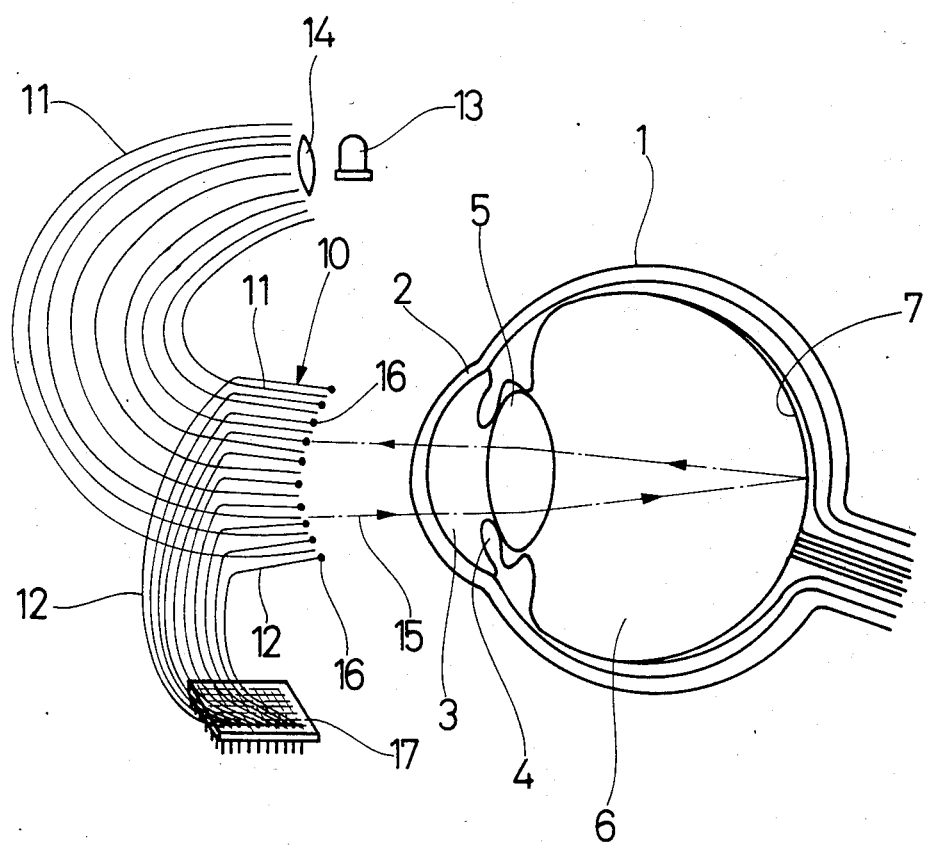
FIG. 1 is a schematic view showing major components of the ophthalmoscopic system according to the present invention.

PARTICULAR DESCRIPTION OF PREFERRED EMBODIMENT:

Referring to the accompanying drawing and first to FIG. 1, indicated at 1 is an eyeball including the cornea 2, fore chamber 3, iris 4, crystalline lens 5, vitreous humour 6 and retina 7. In order to make observation or take a picture of the fundus retina 7, a fibre optics bundle 10 is located directly in front of the cornea 2 without using any light-dispersing or emitting means.

Figure 2:
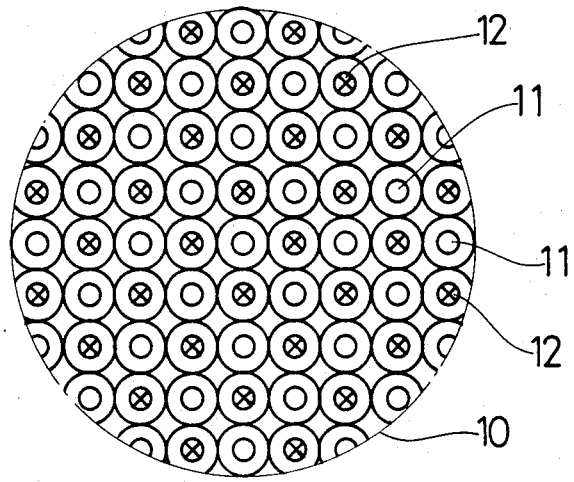
FIG. 2(a) and (b) are schematic views showing the different arrangements of the light transfer and light-receiving fibre optics.
Figure 2:
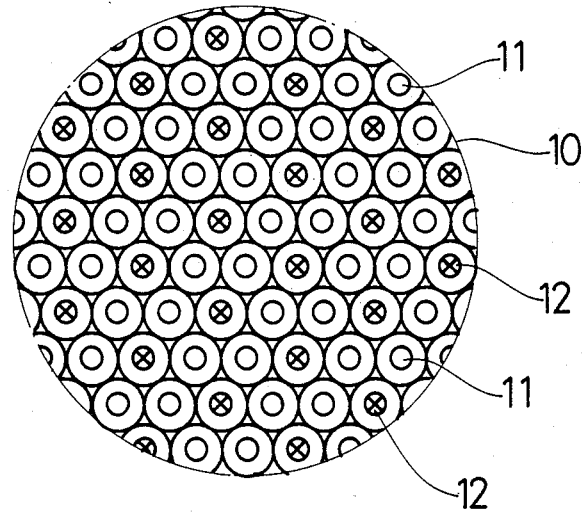
Figure 3:
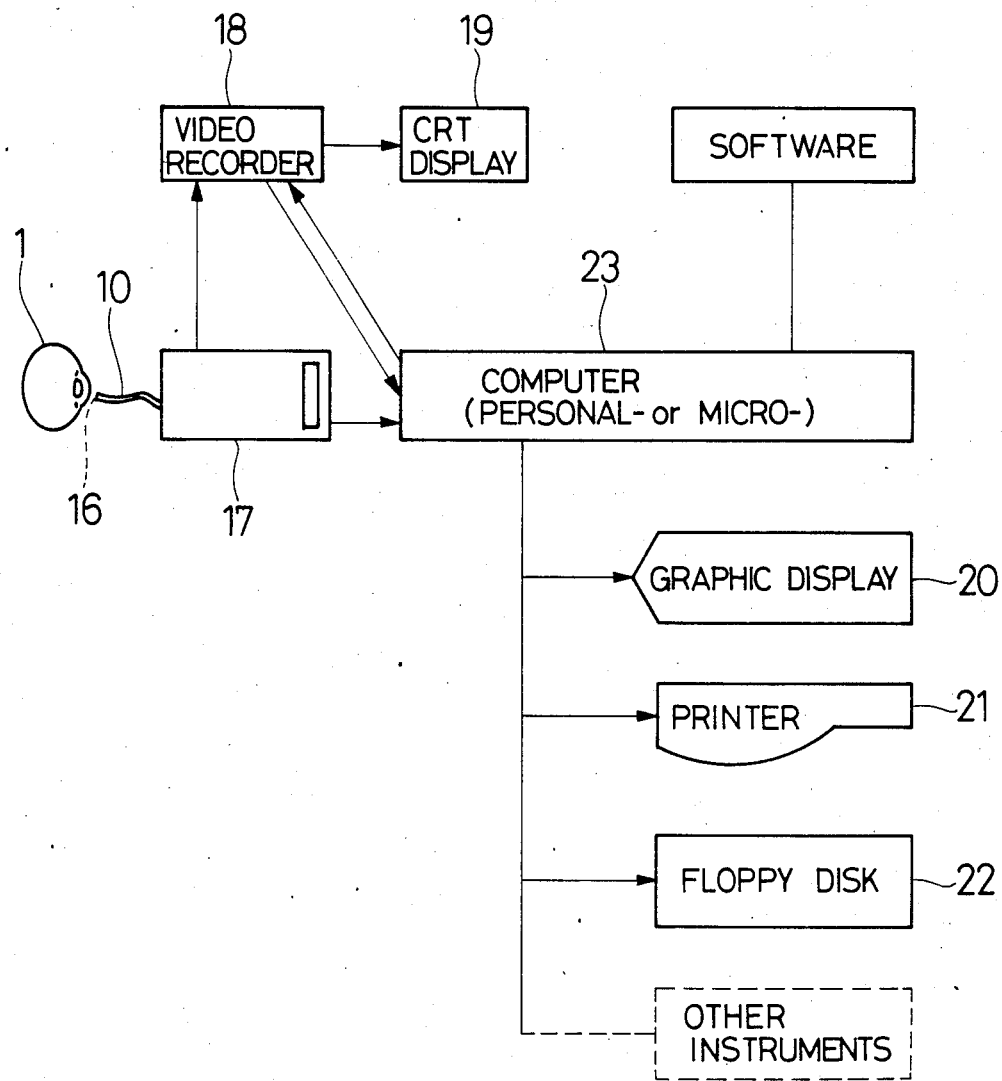
FIG. 3 is a schematic view showing the general construction of the ophthalmoscopic system of the present invention.

The fibre optics bundle 10 consists of a multitude of light transfer fibre optics 11 and light receiving fibre optics 12, each consisting of high quality optical fibre with core and clad (core/clad diameter of about 50–60/125–1000 $\mu$m). The number of the fibre optics filaments is, for example, in the range of 5000–10000 for sending a vivid intraocular image to the semiconductor image conversion element of the image receiver and from the standpoint of reproducing a vivid picture image on a TV or CRT display screen which normally has vertical/horizontal resolution of about 700–2000/5-00–1500. Of course, the number of the fibre optics may be increased to 20000 or 30000 in a case where it is desired to obtain a more vivid picture image by the use of a greater number of fine fibre optics. According to the results of experiments and technical concept of the present invention, it is technically possible to reduce the number of fibre optics to only several tens filaments. In this regard, it is to be noted that, different from the conventional light guide and the energy transfer fibre simply consisting of a bundle of a number of irregularly assembled glass fibre, the multitude of light transfer and light-receiving fibre optics 11 and 12 of the fibre bundle 10 are arranged with a predetermined regularity. In addition, both the light transfer fibre 11 and light-receiving fibre 12 are positioned alternately with each other so that the intraocular image of the patient may be captured with optical accuracy relative to the eyeball of the patient. More specifically, as shown particularly in FIG. 2(a) or (b), the light transfer and light-receiving fibre optics are positioned alternately, the light projecting ends of the fibre optics 11 and the light receiving ends of the fibre optics 12 forming a matrix of regularly arranged discrete points.

The reference numeral 13 denotes a light source for transillumination, which is preferred to employ a semiconductor laser as shown in the drawing or a laser diode, a light emitting diode or other laser light source or an incandescent lamp which is suitable for intraocular examination of the eyeball 1. The light ray from the light source 13 is projected into the light transfer fibre optics 11 through a condenser lens 14 (or directly without passing through a condenser lens). The light rays 15 which were projected from the light transfer fibre optics are reflected on the retina at the fundus and captured by the light receiving fibre optics 12. The ends of the light receiving fibre optics which capture the reflected light rays 15 from the retina 7 may be in a simply cut form or performed with lenses or combined with a condenser lens or a light condensing element 16 for capturing a more vivid picture image of the fundus retina 7 if desired. In a case where the light condensing (light receiving) element 16 is provided, it becomes possible to reduce the number of the light-receiving fibre optics filaments and thus to reduce the diameter of the fibre optics bundle 10 as compared with the case without the light condensing element 16. Of course, the use of a fibre optics bundle of a larger diameter inuser no problems with regard to the performance quality of the system as long as the focal distance and other required optical conditions are satisfied.

The intraocular picture image captured by the light-receiving fibre optics 12 is transferred as it is by the light transmitting characteristics of the light-receiving fibre optics 12 itself, and clearly received by the image receiver 17 which is connected to the other end of the light-receiving fibre optics 12. In this particular embodiment, the image receiver 17 consists of a 12 mm $\times$ 12 mm image conversion element with about 200000 electronic eyes to convert the received light image into electric signals. The output terminal of the image receiver 17 is electrically connected to a video recorder 18 and a CRT 19 of the output system to display the picture image of the fundus retina 7 clearly on the CRT 19. In the particular embodiment shown, a personal computer or a microcomputer 23 with a display 20, a printer 21, a floppy disk 22 with an operating software is connected to the image receiver 17 directly or through the video recorder 18. If desired, the computer 23 may be further connected to a ophthalmographic instrument or a terminal display which is installed in a remote plate to permit simultaneous observation by students or interns.

In order to make an intraocular observation by the above-described system, the light ray from the light source 13 of semiconductor laser or the like is projected into the eyeball 1 through the light transfer fibre optics 11. The incident light 15 is reflected on the fundus retina 7, and the reflected light of the intraocular image is optically captured by the light-receiving fibre optics 12 and thereby transferred to the image receiver 17. After photoelectric conversion at the image receiver 17, the intraocular picture image is recorded in the video recorder 18.

In this instance, a desired light beam can be projected into the eyeball 1 by using a mono-wavelength semiconductor laser as the light source 13. Therefore, it is possible to obtain a vivid and clear intraocular picture image by suitably controlling incident light beam, permitting to improve the accuracy of the ophthalmoscopy to a marked degree. Besides, the illuminant light ray is projected into the eyeball 1 through point-like ends of the individual light transfer fibre optics 11, and the reflected light is received by similarly point-like ends of the light-receiving fibre optics 12, so that the observer can obtain a clear picture image of the whole illuminated intraocular area without being annoyed by reflections of excessive light. Especially, in the particular embodiment shown, it is possible to catch the whole intraocular image more clearly by sequentially projecting the illuminant light at suitable time intervals.

In addition, since the illuminant light is projected in the form of a multitude of discrete light spots and the resulting light reflections are received by a multitude of discrete spots, the oculist or physician can detect the anomalies of intraocular refraction including myopia and hypermetropia by measuring the positions at which the reflected light is received, as well as the troubles in the crystalline lens 5 or vitreous body 6 or the causes of other ocular diseases.

Moreover, as the light transfer fibre optics 11 are arranged to form a multitude of discrete points at their projecting ends, it is possible to reproduce the intraocular picture image vividly by suitably adjusting or selecting the instensity of the light ray to be projected into the fibre, the number and position of illumination, and wavelength of the illuminant light in such a manner as to eliminate the light reflections from the eyeball, coupled with the freedom in the time difference of illumination, permitting to make the fundus observation from various points by arbitrarily setting the angles of incidence and light reception. The above-mentioned intensity of the light ray projected into the eyeball from the light transfer fibre optics, the number and position of illumination, and the wavelength of the illuminant light are adjustable in the following manner. Firstly, the intensity of illuminant light can be adjusting by selecting a suitable luminosity in the case of an incandescent light and by increasing or reducing the amount of light emission in the case of a light emitting element. On the other hand, the number of illumination can be controlled by providing a stop filter in the light path between the light source 13 and the light transfer fibre optics 11 or by intermittently de-actuating the light emitting element at regular time intervals. The position of illumination is adjustable by substantially the same or similar control means. The adjustment of the illuminating position becomes necessary when the examination should be concentrated, for example, to the upper half or the center portion of the eyeball from the clinical viewpoint of a doctor. In such a case, the light source 13 of the light transfer fibre optics 11 surfaces to illuminate only that locality which needs examination. A particular example of the method for adjusting the position of illumination is, in the case of a light source using a light emitting element, to actuate the element particlally to illuminate only the necessary observation area, electrically de-actuating other portions corresponding to the unnecessary areas. When a stop filter is used, it is also arranged to illuminate only the observation area. Further, the wavelength of the illuminant light can be adjusted by changing the kind of the light source 13. For example, in case laser light in the visible ray range is used, the wavelength of the illumination can be adjusted simply by manipulating a dial on the control panel.

The signals of the intraocular picture image which is transmitted to the image receiver 17 through the light-receiving fibre optics 12 in the above-described manner are fed to the video recorder 18 after photoelectric conversion. The video signals of the intraocular picture image, which are recorded in the video recorder 18, are displayed on the CRT 19. In this manner, the optical picture image which is obtained through the light-receiving fibre optics 12 is converted into electric signals at the image receiver 17, it can be reproduced on the CRT clearly in color. Accordingly, it becomes possible for an oculist to make intraocular examinations or observations without any special skill. It also becomes possible to reproduce accumulated diagnostic data of a given patient or a particular case on the display. In case the system includes a computer 23 and its peripheral units including a graphic display 20, a printer 21 and a floppy disk 22 with a suitable operating software, it can realize more comprehensive ophthalmoscopy, judging the nature of an ocular trouble or therapeutic effects by the computer.

As clear from the foregoing description, it is necessary that the fibre optics bundle 10 employed in the ophthalmoscopic system of the invention has the fore ends of the light transfer and light-receiving fibre optics 11 and 12 (or the light condensing element 16) located at a predetermined distance from the cornea 2 of the patient to secure an optical focal length, with the light transfer and receiving fibre optics arranged in regularly alternating positions. The length of the fibre bundle 10 is preferred to be in the range of 1–5 m and normally to be about 3 m in consideration of the compatibility with the patient and other medical equipments. Of course, owing to the excellent light transfer characteristics of the fibre optics, it is possible to transmit a clear picture image over a distance of several hundreds or several thousands kilometers. The fibre optics are preferred to be sheathed in a protective tube to protect their surfaces against damages during use. The light transfer and light-receiving fibre optics are bound into a bundle in regularly alternating positions, forming discrete points at the light projecting and receiving ends as mentioned hereinbefore, except for the terminal ends connected to the light source 13 and the image receiver 17.

It may further be mentioned that the component parts of the ophthalmoscopic system of the invention are commercially available and can be assembled and adjusted by a manufacturer of medical equipments except for certain components which require specific machining or treatments, so that the system can be provided economically at a low cost in spite of its great contribution to the oculist or physician who uses it.

What is claimed is:

1. An opthalmoscopic system, comprising:
   an intraocular illumination light source;
   a fiber optics bundle placed in front of a cornea of an eye, said bundle including a multitude of core and clad type light transfer fiber optics regularly arranged in any direction of the vertical, the horizontal and the oblique to directly project the illuminant light ray from said light source into said eye, without using any specific device for diffusing light or radiation, in the form of a multitude of discrete illuminant light points and said bundle further including a multitude of core and clad type light-receiving fiber optics regularly arranged in any direction of the vertical, the horizontal and the oblique in each of said light transfer fiber optics to receive the reflections of the projected light points;
   a first adjusting means for adjusting the intensity of light ray to be projected into said eye from said light transfer optics, the number and position of illumination and the wavelength of the illuminant light;
   a second adjusting means for adjusting the angle of incidence of the light ray to be projected into the eye from said light transfer fiber optics and the angle of light reception by said light-receiving fiber optics;

an image receiver consisting of a semiconductor image conversion element connected to said light-receiving fiber optics for directly converting a transmitted optical picture image into electric image signals; and an output device, consisting of a single CRT, electrically connected to the output terminal of said image receiver.

2. The ophthalmoscopic system as set forth in claim 1, wherein said light source includes an illuminant selected from the group consisting an illumination lamp, a laser light source, a semiconductor laser, a laser diode and a light emitting diode, in combination with a condenser lens.

3. The ophthalmoscopic system as set forth in claim 1, wherein said output device includes a memory device connected to said image receiver wherein said memory device includes a personal computer or a microcomputer with a display, a printer and a floppy disk.

4. The ophthalmoscopic system as set forth in claim 1, wherein said light transfer fibre optics are adapted to project a light ray into an eye in the form of a multitude of discrete illuminant light points, and said light-receiving fibre optics are adapted to receive the reflection of the projected light ray at a multitude of discrete light-receiving points, converting the received optical image into electric signals at said image converter.

* * * * *